US008377025B2

(12) United States Patent
Nakajima et al.

(10) Patent No.: US 8,377,025 B2
(45) Date of Patent: Feb. 19, 2013

(54) ABSORBENT ARTICLE

(75) Inventors: Kaiyo Nakajima, Kagawa (JP);
Hironao Minato, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 12/921,593

(22) PCT Filed: Dec. 16, 2008

(86) PCT No.: PCT/JP2008/072822
§ 371 (c)(1),
(2), (4) Date: Nov. 21, 2010

(87) PCT Pub. No.: WO2009/113219
PCT Pub. Date: Sep. 17, 2009

(65) Prior Publication Data
US 2011/0060307 A1    Mar. 10, 2011

(30) Foreign Application Priority Data

Mar. 14, 2008    (JP) .................................. 2008-066614

(51) Int. Cl.
*A61F 13/15*    (2006.01)
(52) U.S. Cl. ......... 604/385.25; 604/385.01; 604/385.19; 604/385.26; 604/385.27; 604/385.28; 604/385.29
(58) Field of Classification Search ............. 604/385.01, 604/385.198, 385.25, 385.24, 385.26, 385.27, 604/385.28, 385.29
See application file for complete search history.

(56) References Cited

U.S. PATENT DOCUMENTS 5,062,840 A * 11/1991 Holt et al. ................. 604/385.19
6,458,111 B1 * 10/2002 Onishi et al. ............. 604/385.01
6,700,034 B1 * 3/2004 Lindsay et al. ............... 604/378
(Continued)

FOREIGN PATENT DOCUMENTS

| JP | 2004321460 | 11/2004 |
| JP | 2007105298 | 4/2007 |
| JP | 2007275298 | 10/2007 |
| WO | 2008029923 | 3/2008 |

OTHER PUBLICATIONS

International Search Report for PCT/JP2008/072822 mailed Mar. 17, 2009.
Communication in European Patent No. 08873270.6 mailed Dec. 4, 2012.
Extended European Search Report in Application No. 08873270.6 mailed Nov. 16, 2012.

*Primary Examiner* — Lynne Anderson
*Assistant Examiner* — Bradley Philips
(74) *Attorney, Agent, or Firm* — Lowe Hauptman Ham & Berner, LLP (57) ABSTRACT

An absorbent article includes a void space between a separator sheet and a liquid-absorbent structure. The separator sheet has opposite lateral zones extending in a longitudinal direction, a middle zone via which the opposite lateral zones are contiguous to each other, a front through-hole formed on the side of a front waist region, a rear through-hole formed on the side of rear waist region, and separator sheet biasing elastic members attached under tension to the respective lateral zones. A chassis includes a front leg elastic member laid on the side of the front waist region and a rear leg elastic member laid on the side of the rear waist region wherein at least the rear leg elastic member includes a rear transverse segment extending across the crotch region and a position of the rear transverse segment corresponds to a position of the middle zone of the separator sheet.

17 Claims, 9 Drawing Sheets

U.S. PATENT DOCUMENTS

| | | |
|---|---|---|
| 7,410,479 B2 * | 8/2008 | Hoshino et al. .......... 604/385.27 |
| 2006/0184151 A1 | 8/2006 | Onishi et al. |
| 2007/0088310 A1 * | 4/2007 | Sugiyama et al. ..... 604/385.101 |
| 2007/0233029 A1 * | 10/2007 | Jansson et al. ................ 604/380 |
| 2007/0239128 A1 | 10/2007 | Takada et al. |
| 2008/0065036 A1 | 3/2008 | Minato et al. |

* cited by examiner

ABSORBENT ARTICLE

RELATED APPLICATIONS

The present application is a national phase of PCT/JP2008/072822, filed Dec. 16, 2008, and claims priority from, Japanese Application Number 2008-066614, filed Mar. 14, 2008.

TECHNICAL FIELD

The present invention relates generally to absorbent articles and particularly to absorbent articles such as disposable diapers, toilet-training pants or incontinent briefs.

RELATED ART

Absorbent articles in the form of disposable diaper are known, for example, from JP2007-105298A. According to the disclosure of JP2007-105298A, the diaper comprises a chassis, an absorbent structure provided on an inner surface of the chassis facing the wearer's skin and a skin-contact sheet provided on the inner surface of the absorbent structure facing the wearer's skin. The skin-contact sheet is formed with a through-hole for passage of urine and a through-hole for passage of feces so as to be arranged in a longitudinal direction and defined by the middle region. The skin-contact sheet is further provided along these through-holes with elastic members extending in the longitudinal direction and attached under tension to the skin-contact sheet so that the skin-contact sheet may be spaced upward from the liquid-absorbent structure under contraction of the elastic members. The chassis is provided with leg elastic members attached under tension thereto. Urine and feces are respectively guided through the associated through-holes toward the absorbent structure and thereby the wearer's skin is protected from contact with urine and feces.
PATENT DOCUMENT 1: JP 2007-105298 A

DISCLOSURE OF THE INVENTION

Problem to be Solved by the Invention

Figure 9:
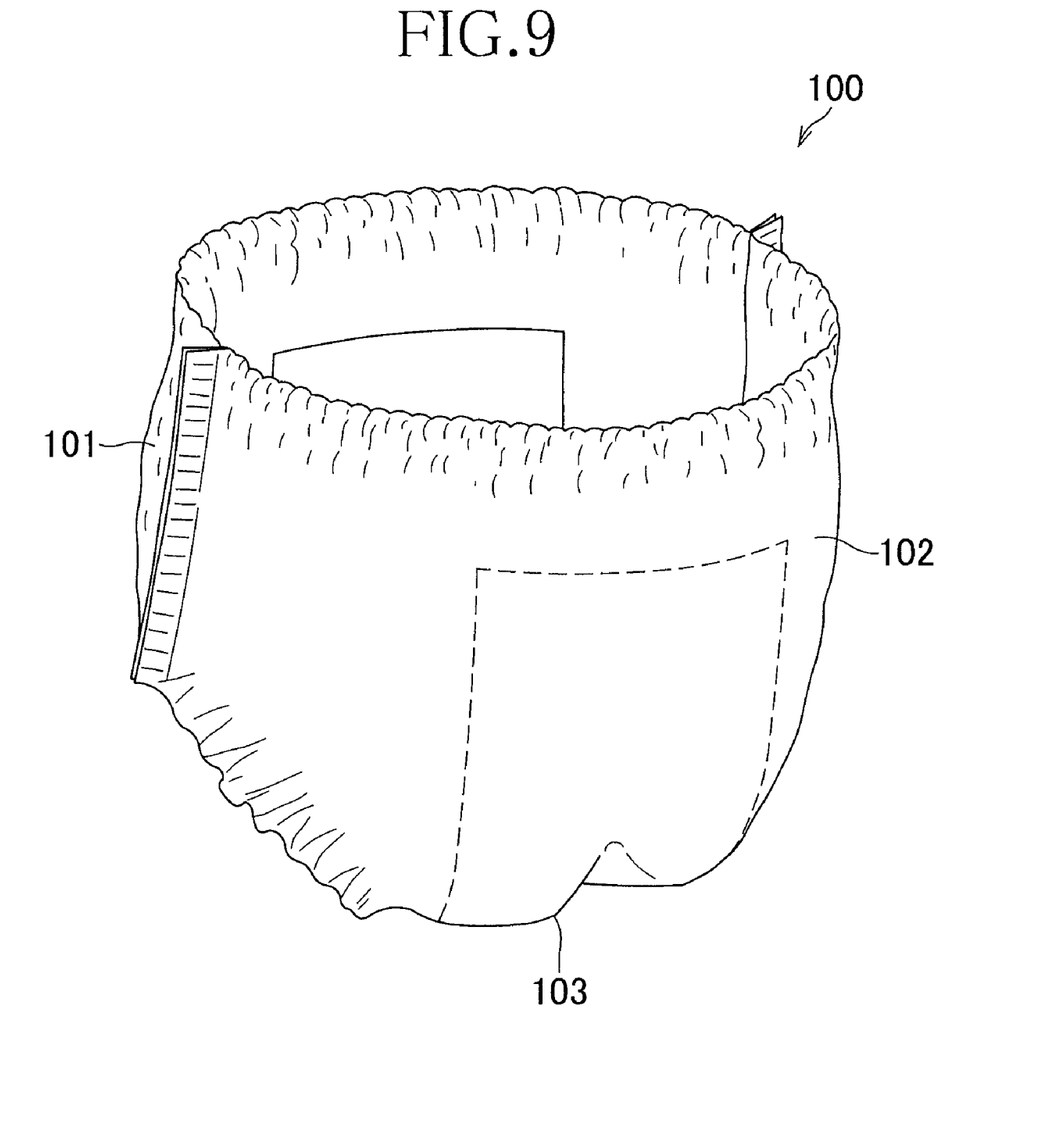
FIG. 9 Schematic diagram exemplarily illustrating the diaper of prior art.

According to the disclosure thereof, the leg elastic members are interrupted in the vicinity of a longitudinal center line bisecting a transverse dimension of the diaper so that neither stretching force nor contractile force of these elastic members is exerted on the diaper in the vicinity of the longitudinal center line. In consequence, the diaper can not maintain its desired shape, for example, when the diaper is subject to external force as the wearer stands up and sits down. In the accompanying drawings, FIG. 9 illustrates such known diaper 100 as put on the wearer's body. The diaper 100 comprises a front waist region 101, a rear waist region 102 and a crotch region 103. Being subject to any external force, the crotch region 103 collapses toward the wearer's body and can not restore its initial shape. With the crotch region 103 having collapsed in this manner, the skin-contact sheet might be left in contact with the chassis and urine and/or feces retained by the absorbent structure provided on the chassis might come in contact with the wearer's skin via the through-hole for passage of urine and/or the through-hole for passage of feces. If urine and/or feces remain in contact with the wearer's skin, the wearer might suffer from skin trouble such as eczema. The skin trouble is serious when feces remain in contact with the wearer's skin.

It is an object of the present invention to define a void space adapted to retain feces between a separator sheet and the liquid-absorbent structure and to maintain this void space.

Measure to Solve the Problem

According to the present invention, there is provided an absorbent article comprising a chassis having a longitudinal direction, a transverse direction, a side facing the wearer's skin, a side facing a wearer's garment, a front waist region, a rear waist region and a crotch region being contiguous one to another in the longitudinal direction and having a liquid-absorbent structure provided at least in the crotch region, and a separator sheet provided on the side facing the wearer's skin of the chassis and being able to be spaced from the chassis in the crotch region wherein the front and rear waist regions of the chassis cooperate to form a waist-opening and the crotch region forms a pair of leg-openings.

The present invention is characterized in that the separator sheet comprises lateral zones extending in the longitudinal direction and opposed to each other in the transverse direction, a middle zone via which the lateral zones are contiguous to each other, a front through-hole for passage of urine bordered by the middle zone so as to lie on the side of the front waist region, a rear through-hole for passage of feces lying on side of the rear waist region and separator sheet biasing elastic members opposed to each other in the transverse direction and extending in the longitudinal direction and attached under tension to the separator sheet. The separator sheet has front and rear ends opposed to each other in the longitudinal direction and extending in the transverse direction are permanently bonded to the side of the chassis facing the wearer's skin and a void space is formed between the separator sheet and the liquid-absorbent structure as the liquid-absorbent structure bows about the crotch region toward the front and rear waist regions. The front and rear through-holes are defined by the lateral zones and the middle zone and adapted for passage of body waste into the void space. The chassis includes leg elastic members attached to respective peripheral edges of the leg-openings, the leg elastic members comprising a front leg elastic member laid on the side of the front waist region and a rear leg elastic member laid on the side of the rear waist region. At least the rear leg elastic member includes a rear transverse segment extending across the crotch region and lying so as to overlap the middle zone.

According to one preferred embodiment of the invention, the rear leg elastic member includes a first peripheral segment extending along one of the leg-openings, the rear transverse segment extending from the one of the leg-openings across the crotch region to the other leg-opening and a second peripheral segment extending along the other leg-opening.

According to another preferred embodiment of the invention, the front leg elastic member includes a front transverse segment extending across the crotch region.

According to still another preferred embodiment of the invention, the liquid-absorbent structure comprises a liquid-absorbent core, a sheet used to wrap the liquid-absorbent core and a folding guide adapted to assist the liquid-absorbent structure to be folded convexly toward the side facing the wearer's garment, and the folding guide is formed so as to be put aside from the rear transverse segment of the rear leg elastic member toward the side of the rear waist region.

According to yet another preferred embodiment of the invention, the folding guide comprises a pair of slits extending in the longitudinal direction so that a distance between the slits in the transverse direction is gradually enlarged toward the side of the rear waist region.

According to further another preferred embodiment of the invention, the folding guide comprises a cutout formed by partially cutting out the liquid-absorbent core.

According to one preferred variant of the invention, the liquid-absorbent structure includes a cutout covering sheet adapted to overlap the cutout and bonded to the wrapping sheet for the liquid-absorbent core.

According to another preferred variant of the invention, the middle zone of the separator sheet is placed aside from a transverse center line bisecting a dimension of the separator sheet in the longitudinal direction toward the side of the front waist region.

According to still another preferred variant of the invention, the absorbent article further includes leak-barrier cuffs comprising a pair of sheets opposed to each other in the transverse direction and extending in the longitudinal direction and cuff-biasing elastic members bonded under tension to respective side edges extending in the longitudinal direction wherein the leak-barrier cuffs are provided on the side of the separator sheet facing the wearer's skin on the respective lateral zones thereof.

Effect of the Invention

Of the leg elastic members attached along the peripheral edges of the respective leg-openings, at least the rear leg elastic member includes the rear transverse segment extending across the crotch region so that the crotch region may be biased by a contractile force of the rear leg elastic member toward the wearer's skin. The zone of the crotch region in which the rear transverse segment is absent is not biased to the wearer's skin and relatively sags down toward the wearer's garment so as to form the pocket. The pocket receives and retains feces and prevents the wearer's skin from contacting with feces. Contractile force of the rear leg elastic member serves also to maintain the chassis sufficiently biased in the crotch region to maintain the shape of the pocket and the initial volume of the void space. The rear transverse segment of the rear leg elastic member extends just on the middle zone of the separator sheet or in the vicinity thereof and consequentially the rear through-through hole is well aligned with the pocket so that the pocket can reliably receive and retain feces.

The rear leg elastic member comprises the first peripheral segment extending along one of the leg-openings, the rear transverse segment extending from the one of the leg-openings across the crotch region to the other leg-opening and the second peripheral segment extending along the other leg-opening. With such unique arrangement, contractile force of the first and second peripheral segments serves to keep the leg-openings in close contact with the wearer's legs. In addition, the shape of the pocket is well maintained by contraction of the first and second peripheral segments in the longitudinal direction and contraction of the transverse segment in the transverse direction.

The front leg elastic member also is provided with the front transverse segment. In this case, the front transverse segment cooperates with the contractile force of the rear transverse segment of the rear leg elastic member to bias the corresponding zone of the crotch region toward the wearer's skin. This biasing effect further facilitates the pocket to be formed and ensures the initial shape of the pocket to be maintained.

The liquid-absorbent structure is provided with the folding guide adapted to assist the structure to be folded so as to become convex toward the wearer's garment. Such folding guide further facilitates the pocket to be formed and to be maintained in its initial shape. The folding guide is formed aside from the rear transverse segment of the rear leg elastic member toward the side of the rear waist region. Such arrangement is effective to guide feces into the pocket and to protect the wearer's skin from contact with feces.

The folding guide comprises a pair of slits extending in the longitudinal direction and a distance between these slits in the transverse direction is gradually enlarged toward the side of the rear waist region. In this way, the liquid-absorbent structure is easily folded on the side of the rear waist region also in the longitudinal direction and the shape of the pocket is further reliably maintained.

In the liquid-absorbent structure, the liquid-absorbent core is partially cut away to form the cutout and the region defined by this cutout has stiffness lower than that in the remaining region and this cutout region can be easily folded toward the wearer's garment to form the pocket. Additionally, even when the liquid-absorbent core absorbs moisture and tends to swell toward the wearer's skin, the cutout prevents the core from swelling and thereby restricts a volume decrease of the void space.

The liquid-absorbent structure includes the cutout covering sheet adapted to overlap the cutout and bonded to the wrapping sheet for the liquid-absorbent core. The cutout covering sheet makes it possible for the liquid-absorbent structure to maintain its stiffness even though the stiffness of the liquid-absorbent structure partially decreases in the region defined by the cutout and the structure temporarily collapses. For example, the void space may collapse under a body weight of the wearer as he or she sits down. If the core is in the state of permanent settling, the flattened void space might not be able to restore the initial volume. However, the cutout covering sheet makes it possible for the flattened void space to restore the initial volume.

The middle zone of the separator sheet is put aside from the transverse center line bisecting the longitudinal dimension thereof toward to the side of the front waist region so that the pocket may be formed aside from the transverse center line toward the rear waist region. With such arrangement, feces can be reliably received and retained in the pocket irrespectively of a differential body shape of the wearer as well as displacement of the article.

The absorbent article further comprises the leak-barrier cuffs and thereby a preventive effect against leak of body waste out from the article is further improved.

IDENTIFICATION OF REFERENCE NUMERALS USED IN THE DRAWINGS 1 diaper
2 chassis 3 separator sheet
7 front waist region
8 rear waist region
9 crotch region
10 liquid-absorbent structure
18 waist-opening
19 leg-opening
21 leg elastic member
23 liquid-absorbent panel (liquid-absorbent structure)
24 liquid-absorbent/dispersant sheet (sheet)
25 liquid-absorbent core
26 liner facing the wearer's skin (sheet)
29 void space
34 front leg elastic member
34a front first peripheral segment
34b front transverse segment
34c front second peripheral segment
35 rear leg elastic member
35a rear first peripheral segment
35b rear transverse segment
35c second peripheral segment
36 cutout
37 lateral zone
38 lateral zone
39 middle zone
40 front through-hole
41 rear through-hole
58 slit (folding guide)

DETAILED DESCRIPTION OF THE PREFERRED EMBODIMENTS

Details of the absorbent article according to the present invention will be more fully understood from the description of disposable diapers as typical embodiments of the inventive absorbent article given hereunder with reference to the accompanying drawings.

First Embodiment

Figure 1:
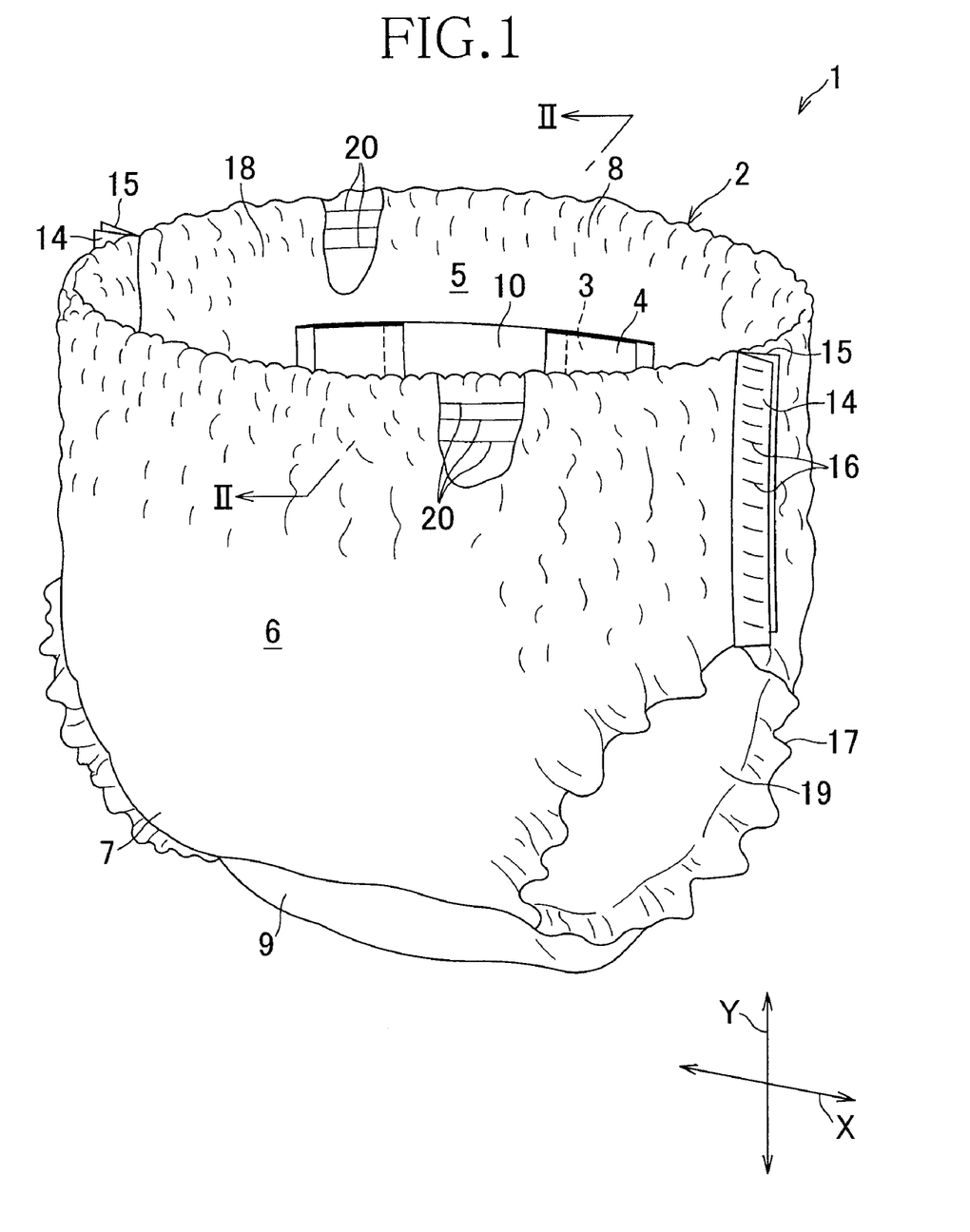
FIG. 1 Perspective view of a diaper according to a first embodiment.

FIGS. 1 through 5 illustrate a first embodiment of the present invention. FIG. 1 illustrates a diaper 1 as put on the wearer's body. As illustrated, the diaper 1 generally comprises a chassis 2, a separator sheet 3 and a pair of leak-barrier cuffs 4. The chassis 2 is pants-shaped and comprises an inner side facing the wearer's skin 5, an outer side facing the wearer's garment 6, a front waist region 7, a rear waist region 8 and a crotch region 9 extending between said front and rear waist regions 7, 8. A direction extending from the front waist region 7 across the crotch region 9 to the rear waist region 8 is referred to herein as a longitudinal direction Y and a direction extending orthogonally to the longitudinal direction Y is referred to herein as a transverse direction X. The chassis 2 is constructed by an inner sheet 11, an outer sheet 12, a barrier sheet 13 sandwiched between these inner and outer sheets 11, 12, and a liquid-absorbent structure 10 laminated on the inner sheet 11.

Opposite side edges 14 of the front waist region 7 and opposite side edges 15 of the rear waist region 8 are put flat and joined together at a plurality of joint streaks 16 arranged intermittently along the respective side edges 14, 15 to form both side seams. Being joined together at the opposite side edges 14, 15, are joint streaks 16, a waist-opening 18 surrounded by the front and rear waist regions 7, 8 is formed and simultaneously a pair of leg-openings 19 respectively having peripheral edges 17. A plurality of waist elastic members 20 extend along the peripheral edge of the waist-opening and a plurality of leg elastic members 21 extend the peripheral edges of the respective leg-openings 19. These elastic members 20, 21 are sandwiched between the inner sheet 11 and the outer sheet 12 and bonded under tension to at least one of these inner and outer sheets 11, 12 by adhesive (not shown).

Figure 2:
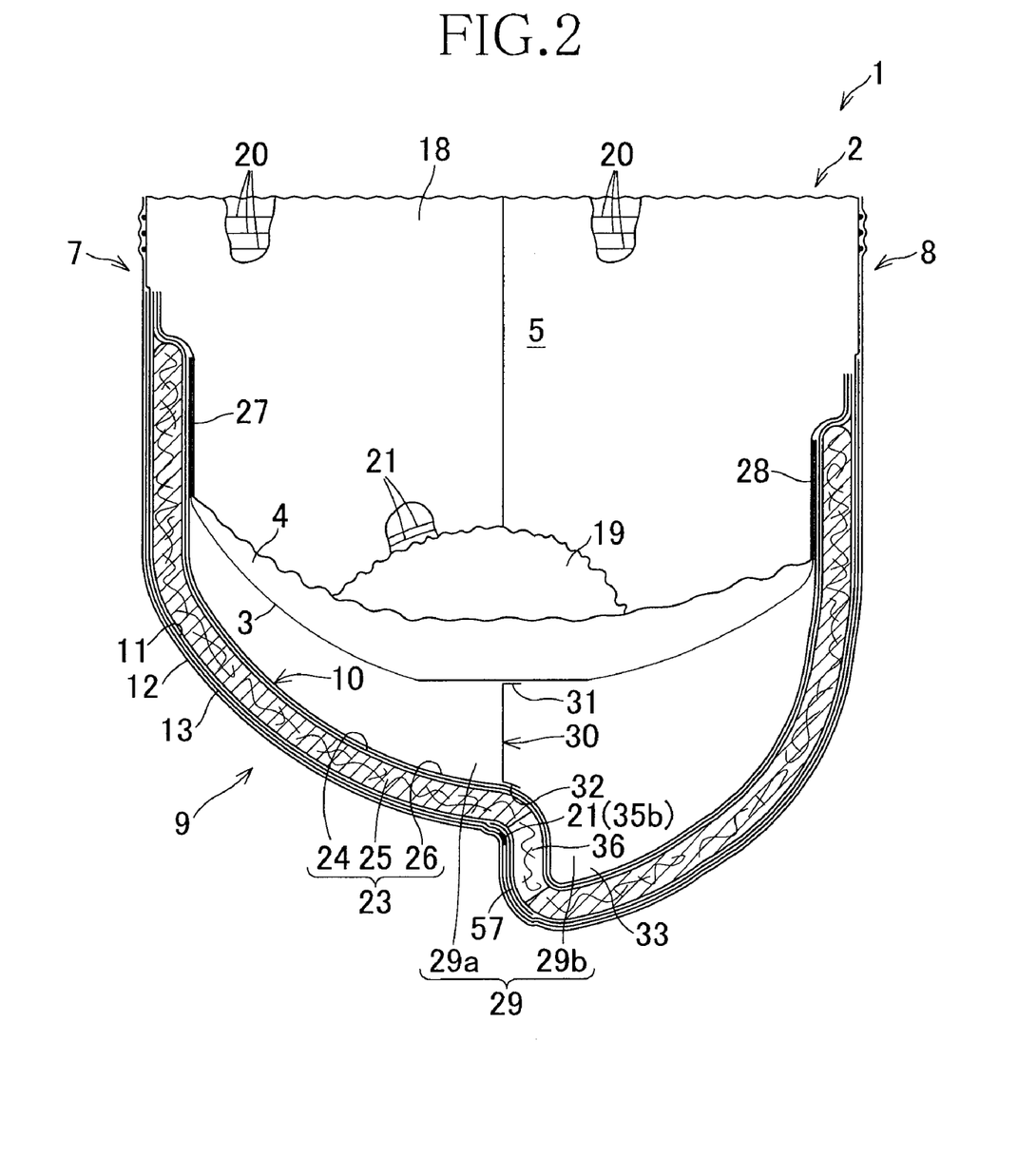
FIG. 2 Sectional view taken along the line II-II in FIG. 1.

FIG. 2 is a sectional view taken along the line II-II in FIG. 1. As will be apparent from FIG. 2, a liquid-absorbent panel 23 constituting the liquid-absorbent structure 10 is provided on the inner side 5 of the inner sheet 11 facing the wearer's skin, the separator sheet 3 is provided aside from the liquid-absorbent structure 10 toward the wearer's skin and the leak-barrier cuffs 4 are provided aside from the separator sheet 3 toward the wearer's skin.

The liquid-absorbent panel 23 comprises a liquid-absorbent core 25 wrapped with a liquid-absorbent/dispersant sheet 24 which is, in turn, covered with a liner 26 facing the wearer's skin. A side of the liquid-absorbent panel 23 facing the wearer's garment is covered with the leak-barrier sheet 13 provided on the inner side of the outer sheet 12 to prevent bodily fluids once absorbed by the core 25 from leaking out from the diaper 1. If it is desired, the leak-barrier sheet 13 may be bonded directly to the bottom surface of the liquid-absorbent panel 23.

The separator sheet 3 is joined in the vicinity of its front and rear ends 27, 28 to the liner 26 facing the wearer's skin by adhesion or welding. The front and rear ends 27, 28 respectively lie in the front and rear waist regions 7, 8. In a pants-shaped state as illustrated, the separator sheet 3 is spaced upward from the liner 26 facing the wearer's skin as a result of bowing of the crotch region 9 and contraction of separator sheet biasing elastic members which will be described later. With the front and rear ends 27, 28 of the separator sheet 3 being joined to the liner 26 facing the wearer's skin, the separator sheet 3 as a whole looks now like a hammock slung. Consequentially, a void space 29 is defined between the separator sheet 3 and the liquid-absorbent panel 23.

A partition sheet 30 vertically extends between the separator sheet 3 and the liquid-absorbent panel 23 to divide the void space 29 into front and rear halves. The partition sheet 30 has vertically opposite upper and lower ends 31, 32 wherein the upper end 31 is joined to the separator sheet 3 by adhesion or welding and the lower end 32 is joined to the liner 26 facing the wearer's skin of the liquid-absorbent panel 23 by adhesion or welding. In this way, the void space 29 can be divided into the front and rear halves 29a, 29b of the void space. The rear half 29b of the void space is convexly expanded downward under a contractile force of the leg elastic members 21 to define a pocket 33.

Figure 3:
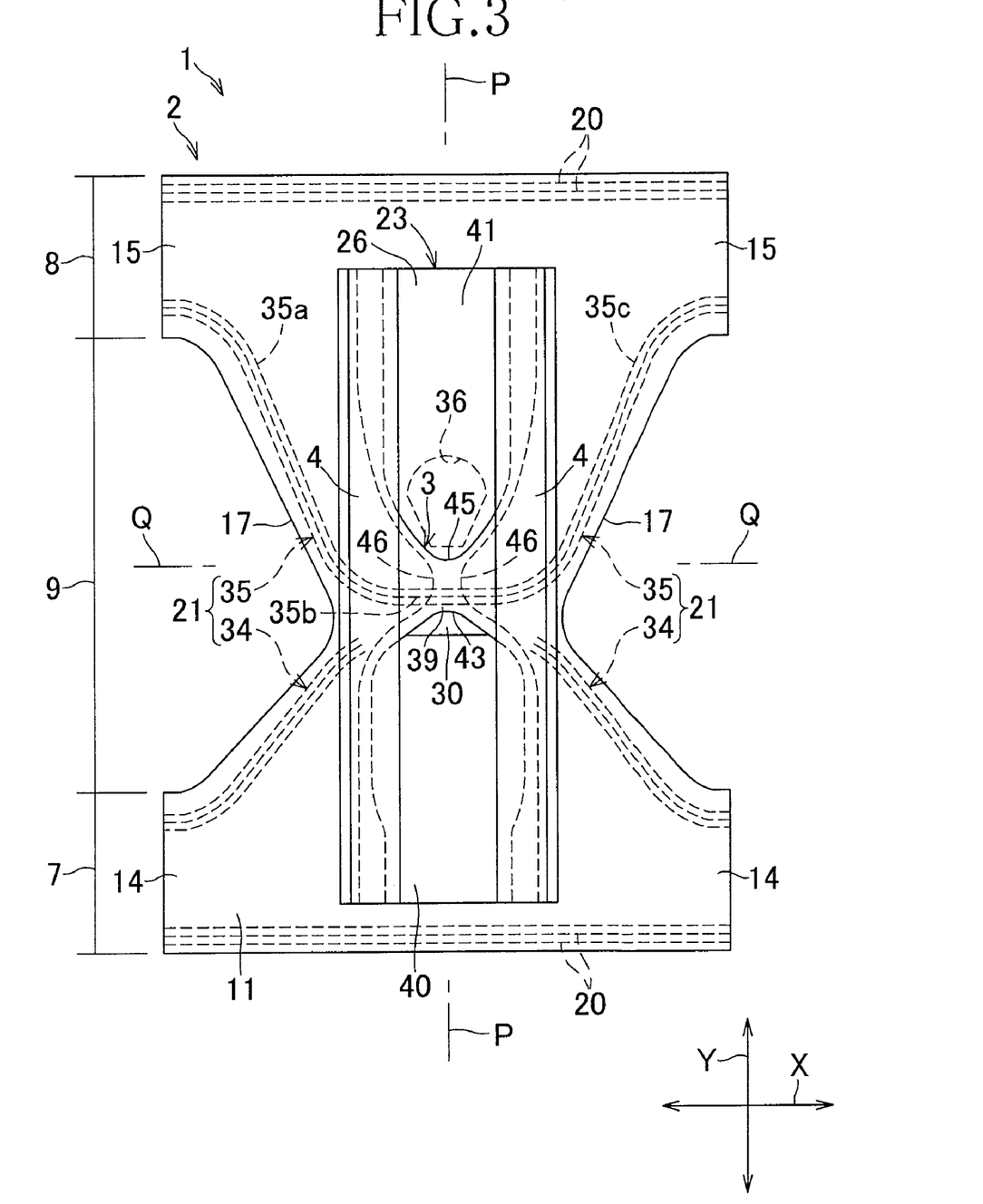
FIG. 3 Plan view of the diaper.

FIG. 3 is a plan view of the diaper 1 wherein the front and rear waist regions 7, 8 have been peeled off from each other at the joint streaks 16 shown in FIG. 1 and then the diaper 1 has been developed and flattened in the longitudinal direction Y as well as in the transverse direction X so that the front and rear waist regions 7, 8 and the crotch region 9 may be coplanar. In this state of the diaper 1, the elasticity of the respective elastic members is supposed to be inactive. The diaper 1 has a longitudinal center line P-P bisecting a dimension thereof in the transverse direction X and a transverse center line Q-Q bisecting a dimension thereof in the longitudinal direction Y. The diaper 1 is bilaterally symmetric about the longitudinal center line P-P.

Figure 4:
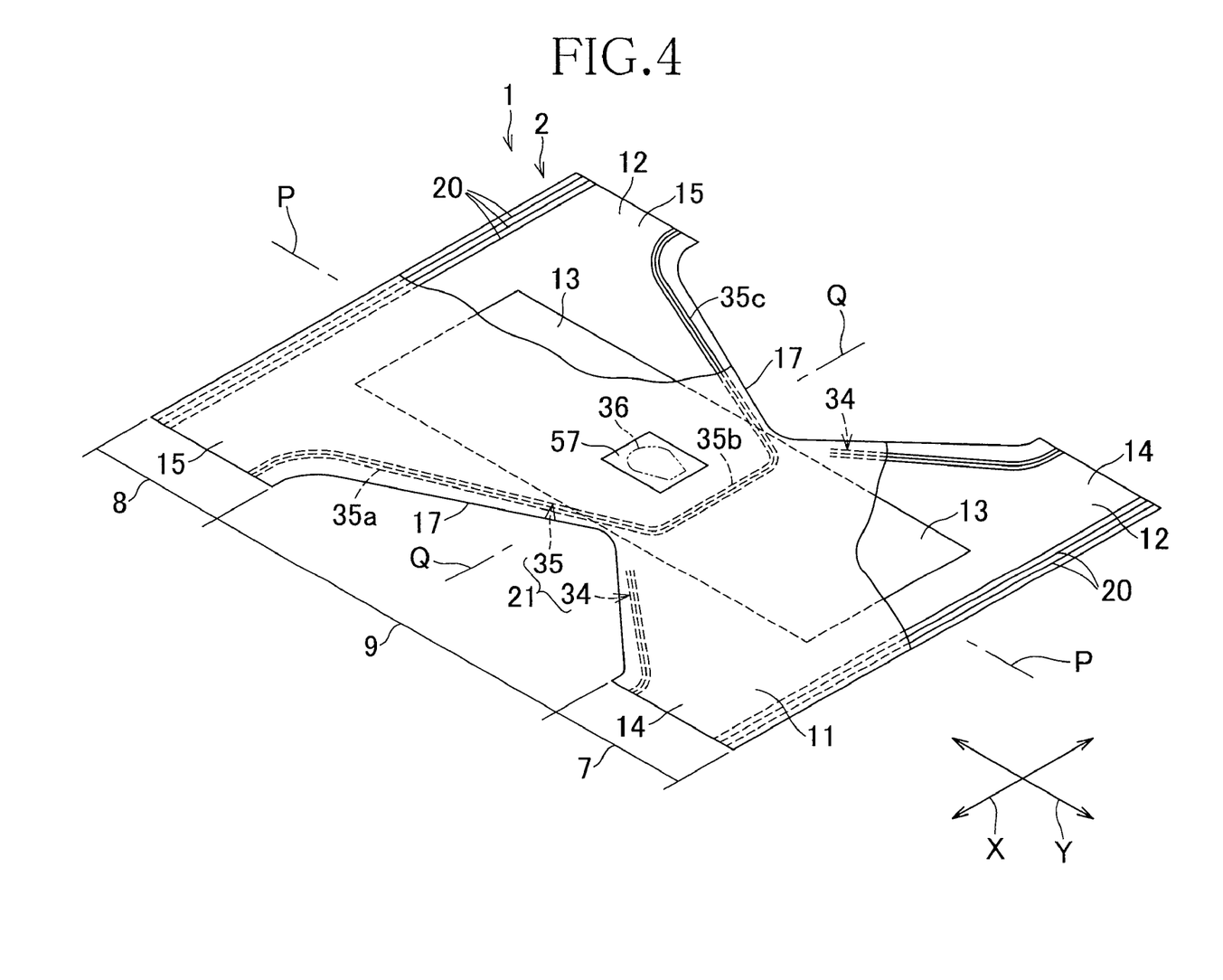
FIG. 4 Explanatory diagram of the diaper.

FIG. 4 is a partially cutaway perspective view illustrating the diaper 1 of FIG. 3 having the liquid-absorbent panel 23 and the other component removed. As illustrated, the chassis 2 includes the inner and outer sheets 11, 12 which are substantially the same in shape as well as in size, the transversely opposite side edges 14, 14 and 15, 15 of the front and rear waist regions 7, 8 and transversely opposite leg-surrounding side edges 17, 17 each extending between the side edge 14 of the front waist region 7 and the side edge 15 of the rear waist region 8. The leg-surrounding side edges 17, 17 convexly curve toward the longitudinal center line P-P.

The inner and outer sheets 11, 12 are formed, for example, by an air-permeable and hydrophobic nonwoven fabric and joined to each other by adhesion or welding.

The leg elastic members 21 comprises a front leg elastic member 34 laid in the front waist region 7 and a rear leg elastic member 35 laid in the rear waist region 8. The front leg elastic member 34 comprises a pair of elastic members separated in the transverse direction X and attached under tension in the longitudinal direction Y to the front half of the leg-surrounding side edges 17, 17. The rear leg elastic member 35 comprises a rear first peripheral segment 35a extending along one of the leg-surrounding side edges 17, a rear transverse segment 35b extending from one of the leg-surrounding side edges 17 in the transverse direction X to the other leg-surrounding side edge 17, and a rear second peripheral segment 35c extending from the rear transverse segment 35b along the other leg-surrounding side edge 17 to the rear waist region 8. The rear leg elastic member 35 is continuous from the rear first peripheral segment 35a to the rear second peripheral segment 35c in the transverse direction X wherein the rear first and second peripheral segments 35a, 35c are attached to the chassis under tension in the longitudinal direction Y while the rear transverse segment 35b is attached to the chassis under tension in the transverse direction X of the crotch region 9.

Figure 5:
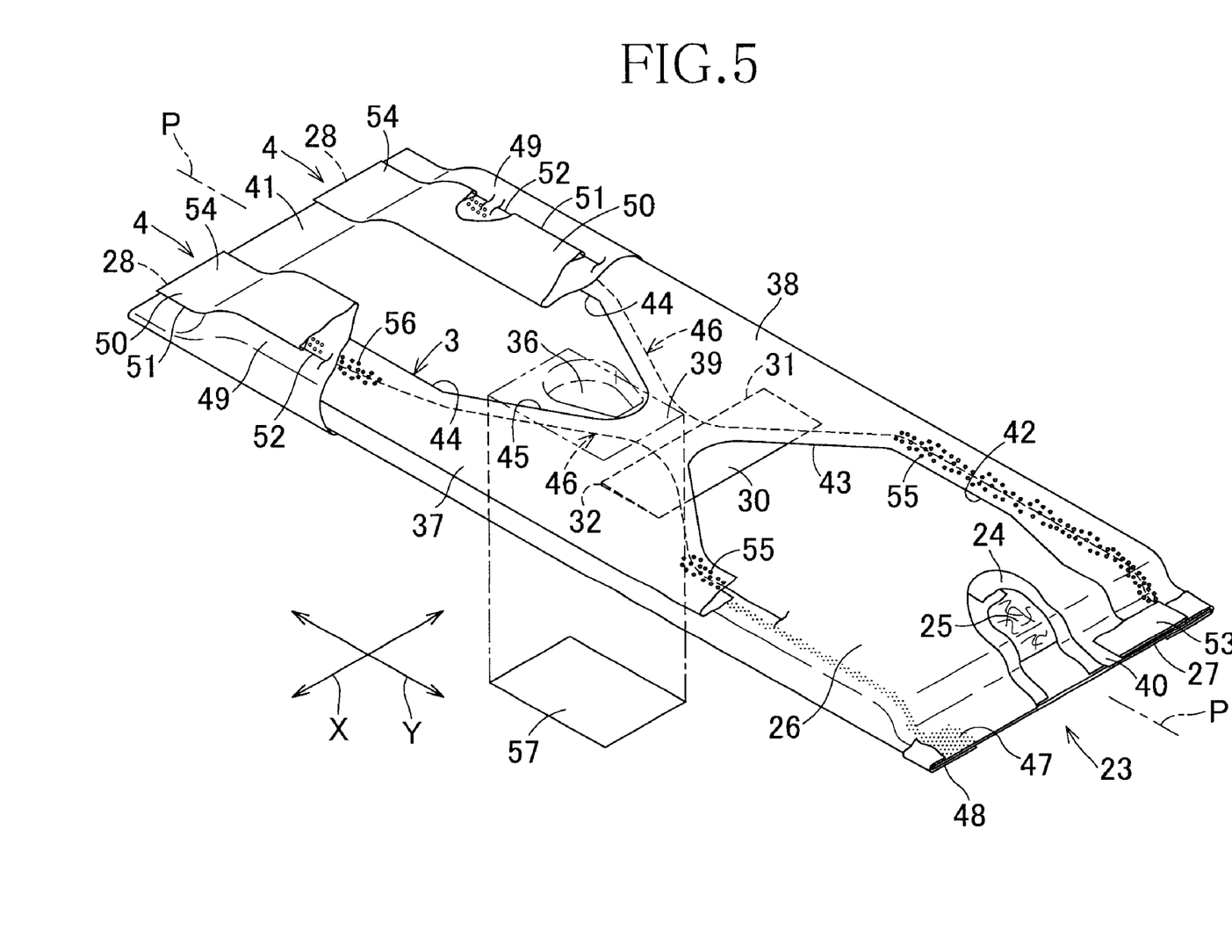
FIG. 5 Explanatory diagram of the diaper.

FIG. 5 is a partially cutaway perspective view basically for the purpose of illustration of the separator sheet 3 and the liquid-absorbent panel 23 wherein the inner and outer sheets 11, 12 shown in FIG. 4 has been eliminated herein for convenience of illustration. As will be seen in FIG. 5, the separator sheet 3 is provided on the inner side of the liquid-absorbent panel 23 facing the wearer's skin and the leak-barrier cuffs 4 are provided on the inner side of the separator sheet 3 facing the wearer's skin.

In the crotch region 9, the liquid-absorbent panel 23 is formed along the longitudinal center line P-P with a cutout 36 serving as a folding guide. The cutout 36 is formed by cutting out from the core 25 and, in this cut out region, the liquid-absorbent/dispersant sheet 24 and the liner 26 facing the wearer's skin both having covered the core 25 now directly overlap each other. The cutout 36 has its dimension in the transverse direction X gradually enlarged from the side of the front waist region 7 toward the side of the rear waist region 8. The liquid-absorbent panel 23 is provided with a cutout covering sheet 57 adapted to overlap the cutout 36. The cutout covering sheet 57 is sandwiched between the liquid-absorbent panel 23 and the inner sheet 11 and joined to at least one of them by adhesion or welding.

The separator sheet 3 comprises a pair of lateral zones 37, 38 opposed to each other in the transverse direction X and a middle zone 39 by which these lateral zones 37, 38 wherein the middle zone 39 lies in the crotch region 9. The lateral zones 37, 38 and the middle zone 39 cooperate to form front and rear through-holes 40, 41. The front through-hole 40 for passage of urine extends from the middle zone 39 to the front waist region 7 substantially in a U-shape and the rear through-hole 41 for passage of feces extends from the middle zone 39 to the rear waist region 8 substantially in a U-shape. The front through-hole 40 for passage of urine is defined by respective inner side edges 42 of the lateral zones 37, 38 and a curved margin of closure 43 making the inner side edges 42 contiguous to each other. The rear through-hole 41 for passage of feces is defined by respective inner side edges 44 of the respective lateral zones 37, 38 and a curved margin of closure 45 making the inner side edges 44 contiguous to each other.

The separator sheet 3 is provided with a pair of separator sheet biasing elastic members 46 extending in the longitudinal direction Y along the front and rear through-holes 40, 41 and attached under tension to the separator sheet 3. The separator sheet biasing elastic members 46 are attached to the separator sheet 3 in a substantially symmetrical relationship about the longitudinal center line P-P and are curved in the vicinity of the middle zone 39 toward the longitudinal center line P-P.

The separator sheet 3 has the opposite lateral zones 37, 38 are folded toward the side of the liquid-absorbent panel 23 in a two-ply fashion. The separator sheet biasing elastic members 46 are sandwiched between these two-ply layers of the lateral zones 37, 38 and bonded thereto by adhesive (not shown). The separator sheet 3 is bonded to the liner 26 facing the wearer's skin of the liquid-absorbent panel 23 by adhesive 47 at least at the front and rear ends 27, 28 of the lateral zones 37, 38 folded in a two-ply fashion. The partition sheet 30 vertically extends between the separator sheet 3 and the liner 26 facing the wearer's skin. As viewed in the transverse direction X, the partition sheet 30 at least extends to straddle the opposite lateral zones 37, 38.

The leak-barrier cuffs 4 comprise a pair of sheets extending in the longitudinal direction Y symmetrically about the longitudinal center line P-P. This sheet may be formed, for example, by a nonwoven fabric or plastic film preferably of liquid-impervious nature. The leak-barrier cuffs 4 are provided so as to overlap the respective lateral zones 37, 38 of the separator sheet 3.

Each of the leak-barrier cuffs 4 comprises a three-ply sheet having a Z-shaped cross section. More specifically, the leak-barrier cuff 4 comprises a first layer 48 sandwiched between the liquid-absorbent panel 23 and the chassis 2 and bonded to the inner sheet 11 of the chassis 2, a second layer 49 folded back from the first layer 48 onto the side of the separator sheet 3 facing the wearer's skin so as to be placed upon the lateral zone 30 or 31 and a third layer 50 folded back onto the side of the second layer 49 facing the wearer's skin. The third layer 50 is folded back onto itself along a side edge 51 thereof so that a cuff biasing elastic member 52 is able to be attached thereto. The cuff-biasing elastic member 52 is wrapped with this side edge 51 folded back in this manner and attached under tension thereto so as to extending in the longitudinal direction Y.

At front and rear ends 53, 54 of the leak-barrier cuff 4, the first, second and third layers 48, 49, 50 are bonded one to another and collectively bonded to the inner sheet 11 of the chassis 2. Under contractile force of the cuff biasing elastic member 52 exerted on the leak-barrier cuff 4, the second layer 49 and the third layer 50 are unfolded upward and thereby spaced from the separator sheet 3 so as to form the wall as seen in FIG. 2. The separator sheet 3 and the leak-barrier cuffs 4 are joined together along front and rear joint zones 55, 56 both provided so as to overlap the separator sheet biasing elastic members 46.

In such combination of the separator sheet 3 and the chassis 2, the middle zone 39 of the separator sheet 3 is put aside from the transverse center line Q-Q toward the front waist region 7, as illustrated in FIG. 3. In consequence, the pocket 33 is formed aside from the transverse center line Q-Q toward the rear waist region 8, ensuring that feces can be received in the pocket 33 irrespectively of any differential body shape among the wearers and any displacement of the diaper.

On the separator sheet 3 as well as the leg elastic members 21 attached to the inner and outer sheets 11, 12, the rear transverse segment 35b of the rear leg elastic member 35 passes across the middle zone 39 of the separator sheet 3. In other words, in the flatly developed state of the diaper as in FIG. 3, the rear leg elastic member 35 overlaps the middle zone 39. However, it is not essential to place the transverse segment 35b just upon the middle zone 39 but it is also possible to achieve the object of the invention by placing the transverse segment 35b within a range at a distance of about 10 mm from the margin of closure 43 of the front through-hole 40 for passage of urine defining the middle zone 39 toward the side of the front waist region 7 and at a distance of about 50 mm from the margin of closure 45 of the rear through-hole 41 for passage of feces toward the side of the rear waist region 8.

With the diaper 1 of such construction now put on the wearer's body, the inner and outer sheets 11, 12 are contracted in the transverse direction X and biased to lift toward the wearer's skin under contraction of the rear transverse segment 35b of the rear leg elastic member 35 (See FIG. 2). In contrast with the regions of the inner and outer sheets 11, 12 directly associated with the rear transverse segment 35b lifted toward the wearer's skin in this manner, the regions of the inner and outer sheets 11, 12 extending on the side of the rear waist region 8 relatively sag down toward the wearer's garment. Obviously the liquid-absorbent panel 23 joined to these inner and outer sheets 11, 12 also sags down toward the wearer's garment. The first and second peripheral segments 35a, 35c contiguous to the opposite ends of the transverse segments 35b bias the inner and outer sheets 11, 12 as well as the liquid-absorbent panel 23 to contract in the longitudinal direction Y and to form the pocket 33 as shown in FIG. 2. The pocket 33 is formed so as to bulge from the rear half 29b of the void space further close to the wearer's garment. The liquid-absorbent panel 23 also sags toward the wearer's garment as the pocket 33 is formed, so the liquid-absorbent panel 23 is reliably prevented from being folded toward the wearer's skin.

The rear transverse segment 35b is laid so as to pass across the middle zone 39 of the separator sheet 3 and, in consequence, the middle zone 39 is lifted toward the wearer's skin while the pocket 33 is formed so as to be opposed to the rear through-hole 41 for passage of feces extending aside from the middle zone 39 toward the side of the rear waist region 8. The diaper 1 must be carefully put on the wearer's body so that the wearer's external genital is opposed to the front through-hole 40 for passage of urine and the wearer's anus is opposed to the rear through-hole 41 for passage of feces. The rear transverse segment 35b extends in the transverse direction X within a range at a distance of about 10 mm from the margin of closure 43 and at a distance of about 50 mm from the margin of closure 45 so that the rear through-hole 41 for passage of feces is reliably opposed to the anus and feces is reliably guided through the rear through-hole 41 into the pocket 33. In this way, the pocket 33 effectively cooperates with the rear half of void space 29b to restrict undesirable contact of feces with the wearer's skin. Should the rear transverse segment 35b be laid at a distance exceeding 10 mm from the margin of closure 43 of the front through-hole 40 for passage of urine, the pocket 33 will be displaced forward from the point of defecation. Should the rear transverse segment 35b be laid at a distance exceeding 50 mm from the margin of closure 45 of the rear through-hole 41 for passage of feces, the pocket 33 will be displaced rearward from the point of defecation. In both cases, it will be impossible to provide the pocket 33 at an appropriate position.

With the diaper 1 put on the wearer's body, the pocket 33 is always biased by the rear leg elastic member 35 and therefore the pocket 33 would not get out of its desired shape. Specifically, even if the pocket 33 gets out of its desired shape due to any external force exerted on the diaper 1, the desired shape of the pocket 33 can be reliably restored under contractile force of the rear leg elastic member 35 once the external force has been removed. In addition to the rear transverse segment 35b, the rear leg elastic member 35 includes the rear first peripheral segment 35a extending along one side edge of the leg-openings 19 and the rear second peripheral segment 35c extending along the other side edge of the leg-opening 19 in the rear waist region 8. Contractile force of these first and second peripheral segments 35a, 35c serve to lift the rear transverse segment 35b further upward and thereby to maintain the desired shape of the pocket 33 further reliably. In this way, feces can be prevented from coming in contact with the wearer's skin more effectively. These first and second peripheral segments 35a, 35c serve also to maintain the leg-openings 19 in close contact with the wearer's legs.

As will be apparent from FIG. 3, the cutout 36 formed in the liquid-absorbent panel 23 is put aside from the rear transverse segment 35b toward the side of the rear waist region 8. The cutout 36 is formed by partially cutting out the core 25 and correspondingly less stiff than the remaining portion. As a result, the region of the core 25 extending beyond opposite side edges of the cutout 36 in the transverse direction X can be easily folded also in the longitudinal direction Y and, under contractile force of the rear transverse segment 35b, the liquid-absorbent panel 23 becomes convex toward the wearer's garment. As the liquid-absorbent panel 23 becomes convex toward the wearer's garment, the desired shape of the pocket 33 can be further reliably restored and the crotch region 9 can be prevent from being permanently collapsed and folded toward the wearer's skin.

While the liquid-absorbent core 25 would otherwise swell toward the wearer's skin as the core 25 absorbs moisture, the cutout 36 formed in the liquid-absorbent panel 23 makes it possible to prevent the core 25 from swelling and thereby to alleviate a volume decrease of the void space 29. While the cutout 36 and the region of the core 25 in the vicinity of this cutout 36 have stiffness inevitably reduced and may result in permanent settling of the core 25, the cutout covering sheet 57 makes it possible to maintain the desired stiffness of the core 25. For example, the void space 29 may collapse under a body weight of the wearer as he or she sits down. If the core 25 is in the state of permanent settling, the flattened void space 29 might not be able to restore the initial volume. However, the cutout covering sheet 57 makes it possible for the flattened void space 29 to restore the initial volume.

While the cutout 36 has been exemplarily described above as the cutout 36 in its entirety is placed aside from the rear transverse segment 35b toward the side of the rear waist region 8, the present invention is not limited to such embodiment. It is also possible to form the cutout 36 in a manner that the cutout 36 partially overlaps the rear transverse segment 35b.

Figure 6:
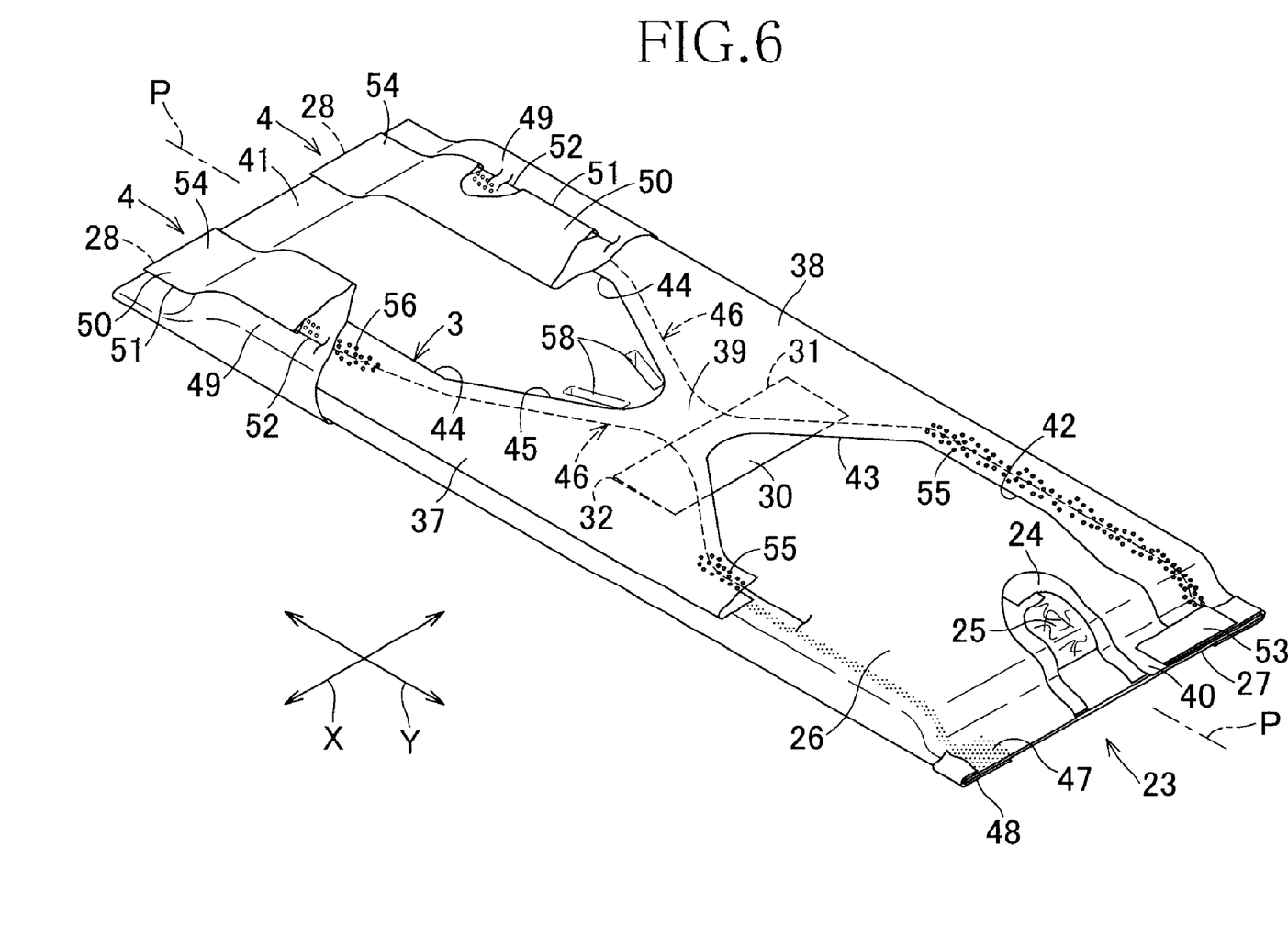
FIG. 6 Explanatory diagram similar to FIG. 5, illustrating another embodiment.

As will be apparent from FIG. 6, it is possible to form a pair of slits 58 extending in the longitudinal direction Y as the folding guide. As shown, these slits 58 are formed by partially removing the liquid-absorbent core 25 in its thickness direction so that a distance between these two slits 58 in the transverse direction X may be gradually enlarged toward the rear waist region 8. These slits 58 facilitate the liquid-absorbent panel 23 to be folded also in the longitudinal direction Y and thereby assist the liquid-absorbent panel 23 to become convex toward the wearer's garment under contractile force of the rear transverse segment 35b. It is possible to provide a single slit 58 extending in the longitudinal direction Y so far as this single split 58 can facilitate the liquid-absorbent panel 23 to be folded in the longitudinal direction Y.

The separator sheet 3 as well as the leak-barrier cuffs 4 may be formed, for example, of a liquid-resistant/air-permeable nonwoven fabric, the inner and outer sheets 11, 12 may be formed, for example, of an air-permeable nonwoven fabric, the leak-barrier sheet 13 may be formed, for example, of a plastic film and the liquid-absorbent panel 23 may be formed, for example, from a mixture of fluff pulp and super-absorbent polymer particles. As stock materials for all of these components, various types of material conventionally used in the relevant technical field may be selectively used.

Second Embodiment

Figure 7:
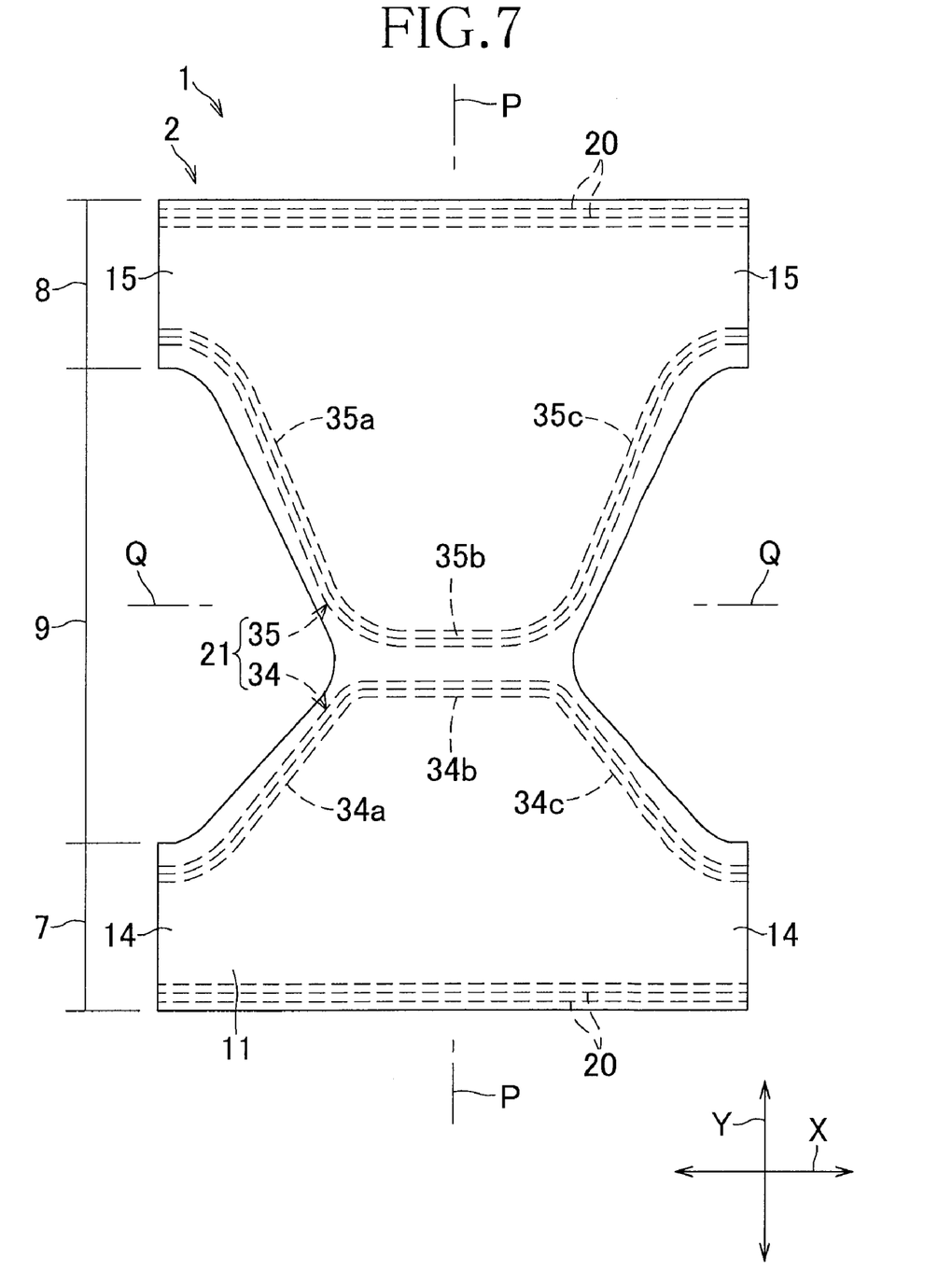
FIG. 7 Explanatory diagram similar to FIG. 4, illustrating a second embodiment.

FIG. 7 is a plan view of a second embodiment of the diaper 1 wherein the liquid-absorbent panel 23, the separator sheet 3 and the leak-barrier cuffs 4 are not shown for convenience of illustration. The second embodiment is similar to the first embodiment except a layout of the front leg elastic member 34, so details of the components similar to those in the first embodiment will not be described here repetitively.

As will be seen in FIG. 7, not only the rear leg elastic members 35 but also the front leg elastic member 34 includes a transverse segment. Specifically, the front leg elastic member 34 comprises a front first peripheral segment 34a extending from the front waist region 7 along one of the leg-surrounding side edges 17, a front transverse segment 34b extending across the crotch region in the transverse direction X from one of the leg-surrounding side edges 17 to the other leg-surrounding side edge 17, and a front second peripheral segment 34c extending from the front transverse segment 34b along the other leg-surrounding side edge 17 toward the front waist region 7. In this manner, the front leg elastic member 34 is laid to extend continuously in the transverse direction X. The rear transverse segment 35b of the rear leg elastic member 35 and the front transverse segment 34b of the front leg elastic member 34 are spaced from each other in the longitudinal direction Y without intersecting each other.

Both the rear leg elastic member 35 and the front leg elastic member 34 have the transverse segments 35b, 34b, respectively, which cooperate to bias the crotch region 9 toward the wearer's skin. In this way, these transverse segments 35b, 34b ensure that the pocket 33 is reliably formed and the pocket 33 reliably maintains its desired shape to prevent the wearer's skin from contacting with feces.

Figure 8:
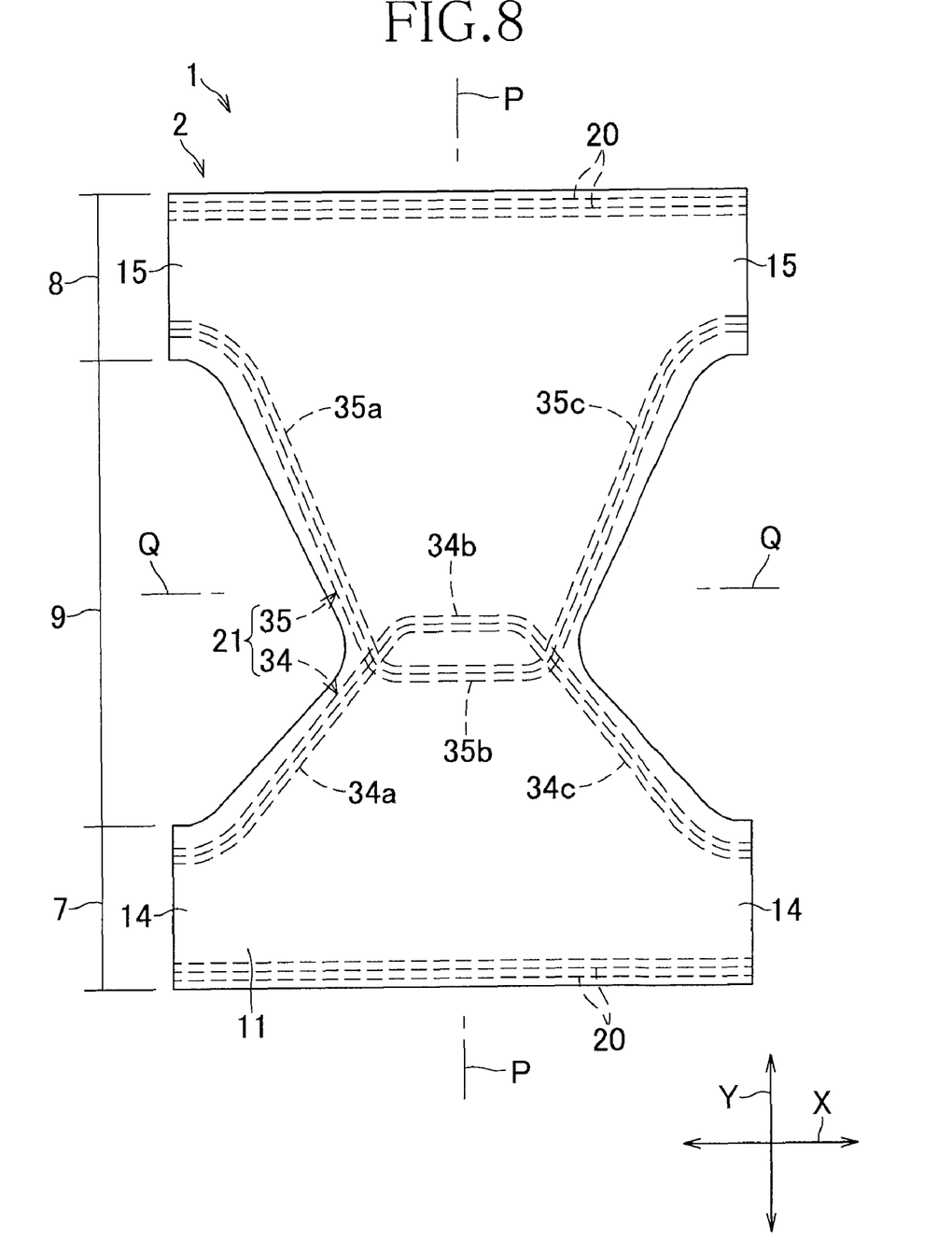
FIG. 8 Explanatory diagram similar to FIG. 7, illustrating another embodiment.

FIG. 8 illustrates a variant of the second embodiment in which the front leg member 34 also includes the transverse segment. In the case illustrated in FIG. 8, the font transverse segment 34b of the front leg elastic member 34 and the rear transverse segment 35b of the rear leg elastic member 35 intersect each other in the crotch region 9. More specifically, the front and rear transverse segments 34b, 35b intersects each other at respective ends opposite in the transverse direction X so that, in the crotch region 9, the front and rear transverse segments 34b, 35b are spaced from each other, i.e., the rear transverse segment 35b lies aside toward the side of the front waist region 7 while the front transverse segment 34b lies aside toward the side of the rear waist region 8.

Also according to this variant in which the front and rear leg elastic members 34, 35 intersect each other as has been described just above, the front and rear transverse segments 34b, 35b cooperate to bias the crotch region 9 toward the wearer's skin sufficiently to prevent the wearer's skin from contacting with feces. The front and rear transverse segments 34b, 35b can be not only spaced from each other as shown in FIG. 8, but also overlap each other.

The invention claimed is:

1. An absorbent article, comprising:
a chassis having a longitudinal direction and a transverse direction, a skin-facing side for facing a wearer's skin and a garment-facing side for facing the wearer's garment,
a front waist region, a rear waist region and a crotch region being contiguous one to another in said longitudinal direction,
a liquid-absorbent structure provided at least in said crotch region, and
a separator sheet provided on said skin-facing side of said chassis and adapted to be spaced from said chassis in said crotch region,
wherein
said front and rear waist regions of said chassis cooperate to form a waist-opening and said crotch region forms a pair of leg-openings,
said separator sheet comprises
lateral zones extending in said longitudinal direction and opposed to each other in said transverse direction,
a middle zone via which said lateral zones are contiguous to each other,
a front through-hole bordered by said middle zone so as to lie on a side of said front waist region,
a rear through-hole lying on a side of said rear waist region, and
separator sheet biasing elastic members opposed to each other in said transverse direction, extending in said longitudinal direction and attached under tension to said separator sheet,
said separator sheet further has ends opposed to each other in said longitudinal direction and extending in said transverse direction, wherein said ends are permanently bonded to said skin-facing side of said chassis,
a void space is formed between said separator sheet and said crotch region when said liquid-absorbent structure bows about said crotch region toward said front and rear waist regions in use,
said front and rear through-holes are defined by said lateral zones and said middle zone and adapted for passage of body waste into said void space,
said chassis includes leg elastic members attached to respective peripheral edges of said leg-openings, said leg elastic members comprising a front leg elastic member laid on the side of said front waist region and a rear leg elastic member laid on the side of said rear waist region,
at least said rear leg elastic member includes a rear transverse segment which is placed toward the front waist region and beyond a transverse center line bisecting a dimension of the chassis in the longitudinal direction,
said liquid-absorbent structure comprises
a liquid-absorbent core,
a sheet wrapping said liquid-absorbent core, and
a folding guide adapted to assist said liquid-absorbent structure to be folded convexly toward said garment-facing side, said folding guide adapted to be oriented generally perpendicular to the separator sheet upon contraction of said rear transverse segment, and
said folding guide is formed between said rear transverse segment of said rear leg elastic member and said rear waist region.

2. The absorbent article as defined by claim 1, wherein said rear leg elastic member includes
- a first peripheral segment extending along one of said leg-openings,
- a second peripheral segment extending along the other leg-opening, and
- said rear transverse segment extending from said first peripheral segment across said crotch region to the second peripheral segment.

3. The absorbent article as defined by claim 1, wherein said front leg elastic member includes a front transverse segment extending across said crotch region.

4. The absorbent article as defined by claim 1, wherein
- said folding guide comprises a pair of slits extending in said longitudinal direction, and
- a distance between said slits in said transverse direction is gradually enlarged toward said rear waist region.

5. The absorbent article as defined by claim 1, wherein said folding guide comprises a cutout arranged in said liquid-absorbent structure.

6. The absorbent article as defined by claim 5, wherein said liquid-absorbent structure includes a cutout covering sheet overlapping said cutout and bonded to said sheet which wraps said liquid-absorbent core.

7. The absorbent article as defined by claim 1, wherein said middle zone of said separator sheet is placed toward said front waist region and beyond the transverse center line bisecting the dimension of said chassis in said longitudinal direction.

8. The absorbent article as defined by claim 1, further comprising
- leak-barrier cuffs that include a pair of sheets opposed to each other in said transverse direction and extending in said longitudinal direction, and
- cuff-biasing elastic members bonded under tension to respective side edges of the leak-barrier cuffs extending in said longitudinal direction,
- wherein said leak-barrier cuffs are provided on said respective lateral zones of said separator sheet to face the wearer's skin in use.

9. The absorbent article as defined in claim 1, wherein the rear transverse segment does not overlap the front and rear through-holes.

10. The absorbent article as defined in claim 5, further comprising
- a partition sheet that extends in a thickness direction of the absorbent article between the separator sheet and the liquid-absorbent structure to divide the void space into front and rear halves, wherein said partition sheet does not overlap the cutout in the liquid-absorbent structure.

11. The absorbent article as defined in claim 10, wherein the rear transverse segment of the rear leg elastic member overlaps the partition sheet in the thickness direction.

12. The absorbent article as defined in claim 3, wherein
- the front transverse segment of the front leg elastic member and the rear transverse segment of the rear leg elastic member extend in the transverse direction without overlapping each other, and
- the front transverse segment and the rear transverse segment are placed toward the front waist region and beyond the transverse center line.

13. The absorbent article as defined in claim 3, wherein the front leg elastic member and the rear leg elastic member overlap each other in the crotch region at locations which are placed toward the front waist region and beyond the transverse center line.

14. The absorbent article as defined by claim 1, further comprising a pair of leak-barrier cuffs opposed to each other in the transverse direction and extending in the longitudinal direction,
- wherein each leak-barrier cuff includes front and rear ends opposite to each other in the longitudinal direction, and is folded to define first, second and third layers.

15. The absorbent article as defined by claim 14, wherein each leak-barrier cuff is folded outwardly to define the third layer that is directly bonded to the second layer at the front and rear ends.

16. The absorbent article as defined by claim 14, wherein the first and second layers are directly bonded to a bottom and a top, respectively, of the sheet wrapping said liquid-absorbent core.

17. The absorbent article as defined by claim 14, wherein each leak-barrier cuff comprises a three-ply sheet including the first, second and third layers that define a Z-shaped cross section or an inverted Z-shaped cross section.

\* \* \* \* \*